United States Patent [19]
Monthony et al.

[11] Patent Number: 5,716,798
[45] Date of Patent: Feb. 10, 1998

[54] ENHANCED DETECTION OF MICROORGANISMS IN SAMPLES

[75] Inventors: James F. Monthony, Baltimore; David T. Stitt, Freeland; Denise H. Burroughs, Baltimore, all of Md.

[73] Assignee: Becton Dickinson and Company, Franklin Lakes, N.J.

[21] Appl. No.: 926,729

[22] Filed: Sep. 22, 1992

[51] Int. Cl.$^6$ ............... C12Q 1/04; C12M 1/00; G01N 21/54

[52] U.S. Cl. ............ 435/34; 435/284; 435/287; 435/296; 435/301; 436/172; 436/805; 436/905; 436/909; 422/82.05; 422/82.07; 422/82.08; 422/85; 422/107

[58] Field of Search .............. 435/34, 284, 287, 435/296, 301; 436/172, 805, 905, 909; 422/82.05, 82.07, 82.08, 85, 102

[56] References Cited

U.S. PATENT DOCUMENTS

| | | | |
|---|---|---|---|
| 4,237,096 | 12/1980 | Popoff et al. | 422/102 |
| 4,245,043 | 1/1981 | Lund | 435/33 |
| 4,299,918 | 11/1981 | Popoff et al. | 435/34 |
| 4,358,203 | 11/1982 | Citrin | 435/34 |
| 4,545,958 | 10/1985 | Dopatha | 422/102 |
| 4,682,891 | 7/1987 | de Macario et al. | 422/102 |
| 4,761,378 | 8/1988 | Godsey | 435/301 |
| 4,772,558 | 9/1988 | Hammann | 435/300 |
| 4,968,623 | 11/1990 | Franks | 435/285 |
| 5,164,301 | 11/1992 | Thompson et al. | 435/34 |
| 5,182,082 | 1/1993 | Monthony et al. | 422/57 |

OTHER PUBLICATIONS

Nir et al, *APMS*, vol. 98, No. 7, pp. 645–651, Jul. 1990.

*Primary Examiner*—Cecilia J. Tsang
*Assistant Examiner*—Abdel Mohamed
*Attorney, Agent, or Firm*—Susan A. Capello

[57] ABSTRACT

This invention describes a method for the rapid identification of the presence of microorganisms in a sample. Briefly, in the method of this invention the sample container is divided into a plurality of discrete zones, each of which can be separately monitored for microbial presence. When a sample is placed into this container, detection is simplified as the volume monitored is low (as compared with the sample); since microbial detection is a concentration dependent phenomenon, the speed with which the presence of microbial contamination can be detected is increased.

8 Claims, 3 Drawing Sheets

# ENHANCED DETECTION OF MICROORGANISMS IN SAMPLES

BACKGROUND OF INVENTION

The detection of microorganisms in samples is generally a time consuming and laborious clinical procedure. In ordinary practice, a small portion of the sample, called an inoculum, is placed onto a media conducive to microbial growth. The system is then incubated under appropriate conditions and, after an appropriate time, the results are read.

Plates are inspected and scored every day. Depending upon the suspected type of organism and the kind of medium used, plates with no growth are generally not discarded for 4 to 8 days. For small volume samples with a fairly high concentration of organism, the procedure above works well. For case where a fairy large liquid sample is required due to a low concentration of viable microorganisms, the sample is diluted with a several fold greater volume of liquid media and the mixture incubated to detect growth. Normally sterile samples such as blood samples being tested for the presence of viable microorganisms may require from 1 to several days before growth can be detected. Bottles are inspected daily. Bottles with no growth are generally not discarded for 5 to 7 days.

Thus, there exists a real need to reduce this incubation time.

SUMMARY OF INVENTION

The above is realized by the method of this invention. Briefly, in the method of this invention the sample container is divided into a plurality of discrete zones, each of which can be separately monitored for microbial presence. When a sample is placed into this container, detection is simplified as the volume monitored is low (as compared with the sample); since microbial detection is a concentration dependent phenomenon, the speed with which the presence of microbial contamination can be detected is increased.

DETAILED DESCRIPTION OF INVENTION

This invention provides a convenient way of enhancing microbial detection, thereby decreasing the detection time required, by dividing the sample into discrete regions and analyzing each separately. Since detection is dependent upon the concentration of the bacteria in the system, analysis of each individual region will provide detection of the bacteria in the system more rapidly, and at a lower overall concentration than analysis of the entire mixture.

By way of example, the BACTEC® blood culture analyzer system marketed by Becton, Dickinson and Company requires an approximate threshold concentration of $1 \times 10^6$ organisms/ml to yield a positive result. If an initial inoculum, diluted to 50 ml with culture media contained only 1 CFU (0.02 CFU/ml), it can be calculated that a total of 26 generations would be required to achieve this threshold concentration. One Organism would have to multiply to more than $5 \times 10^7$ organisms. At an average generation time of 30 minutes, this translates to a detection time of 13 hours (assuming no lag before growth starts).

In a preferred embodiment of this invention, the 50 ml sample is divided into 100 regions of 0.5 ml each. To achieve an effective concentration of $1 \times 10^6$ CFU/ml, such a region would need an actual concentration of $5 \times 10^5$ CFU/ml. This would be achieved in 19 generations in the cell containing the organism or about 9.5 hours (assuming the same generation time and no time lag as above), translating to a 3.5 hour saving. Should the 50 ml sample be divided into 1000 regions of 0.05 ml each, then only 16 generations or 8 hours would be required for each organism to multiply to greater than $1 \times 10^6$ CFU/ml.

It is easily recognized that the number of regions examined and the volume of these regions can be varied as particular applications or equipment restrictions dictate. Further the means of achieving this division is immaterial, so long as the regions are effectively isolated from each other.

Figure 1A:
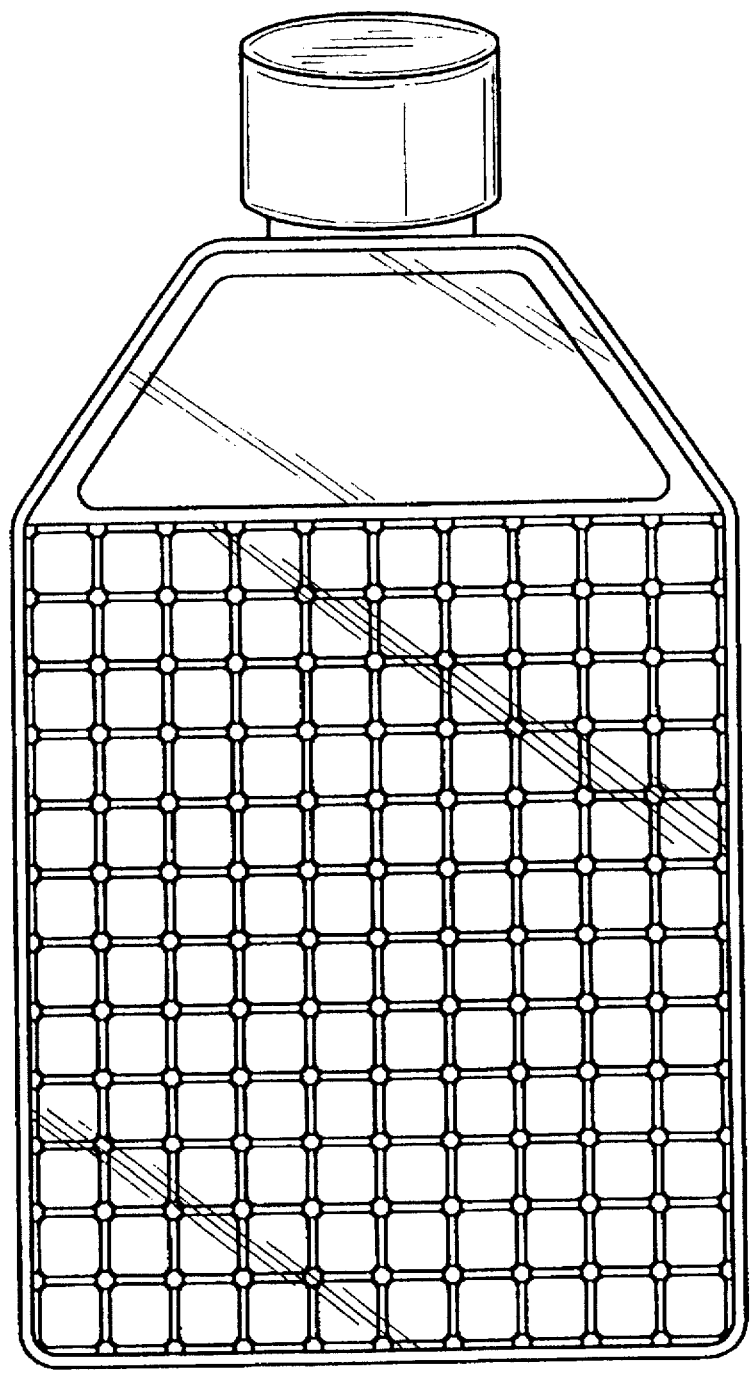
FIGS. 1(a) and 1(b) present preferred apparatus for the division of the sample into a plurality of regions by use of interlocking dividers; 1(a) shows the device through one face, 1(b) presents a side view, and 1(c) presents a detail of the interlocking dividers.
Figure 1B:
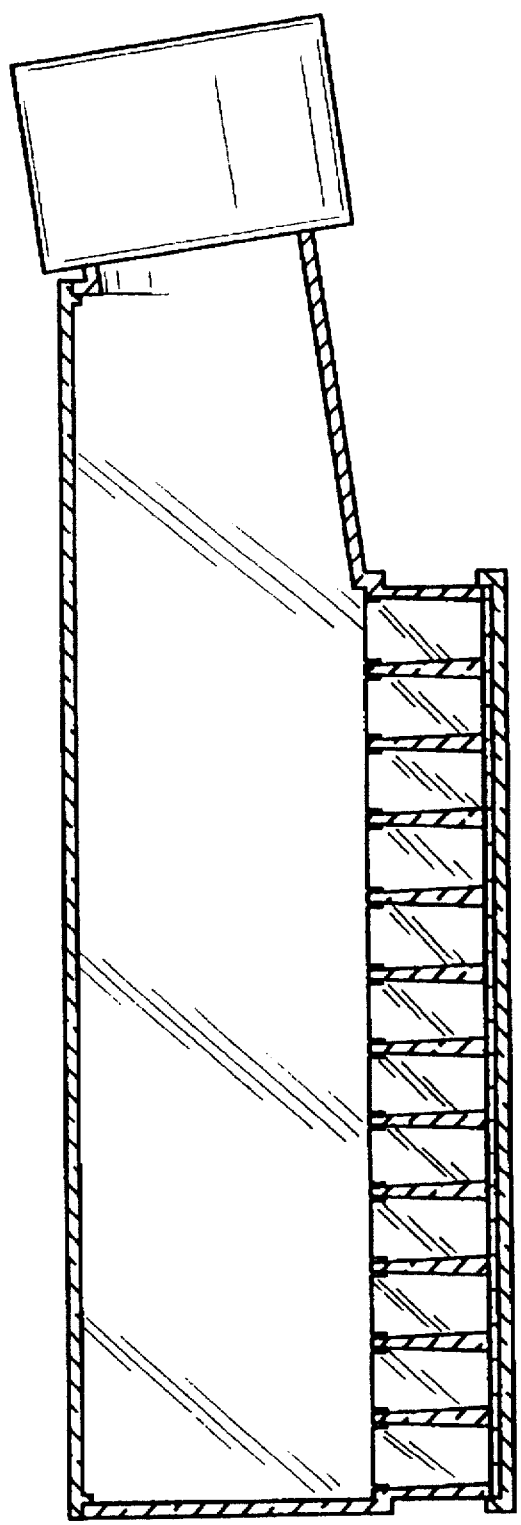
Figure 1C:
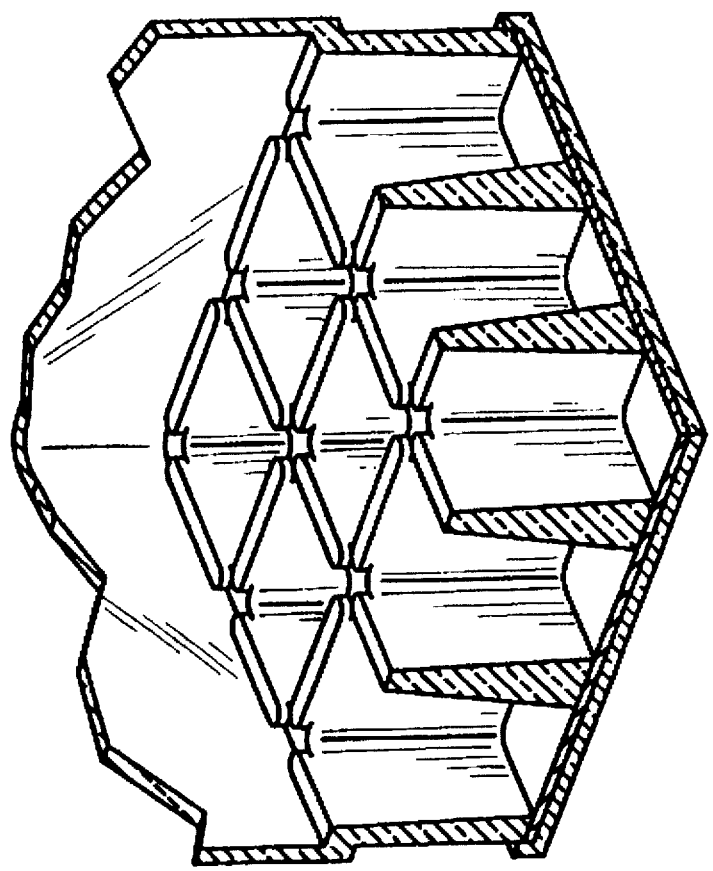

FIG. 1 shows a preferred apparatus for this division, comprising a culture bottle divided on one face into a plurality of regions by interlocking dividers. These form discrete regions in the form of parallelapipeds, each having an identical volume. In actual use the height of these dividers must be sufficient to fully contain the volume during incubation, including incubation on an agitating device such as a shaker, when used.

In practice the inoculum is introduced into the bottle which is then laid on the face containing the divider to obtain the division of the sample into the separate regions. The bottle is then incubated and analyzed for growth by any convenient means. Preferred methods of analysis include colorimetric, fluorometric, radiometric, nephelometric, and infrared analyses.

It is to be recognized that the shape and/or volume of the regions can be varied, although identical shapes and volumes for each region are preferred.

In addition to rapid detection of microorganisms, this method has two other major advantages over the prior art. The first is that this method permits quantitation of the bacteremia or septicemia. The second is that the method is both compatible with polymicrobial specimens and the method will, under most circumstances, produce isolated cultures from mixed specimens as long as the initial level of organisms is low.

The Isolator 7.5 Microbial Tube marketed by Wampole Laboratories is a device and a system for concentrating microorganisms from blood specimens by centrifugation. The method is very time and labor intensive, including over a 25 step procedure with a 30 minute centrifuge spin. This method has been widely accepted, in part because it is the only commercial method capable of estimating the number of organisms in the original blood sample. An evaluation of this method by Dorn et al. (J. Clin. Micro., 9, pp. 391–396) concluded "Quantitation, offered only by the centrifugation method, proved useful on several occasions in discriminating between an opportunistic infection versus a skin contaminant and in judging the efficacy of antimicrobial therapy." Sullivan et al (Pediatrics, 69, 699–702) have demonstrated that the magnitude of bacteremia in children is associated with the severity of clinical disease.

In the method of this invention, the estimation of the number of microorganisms in the original sample is as easy as counting the number of regions which have shown growth. When the number of positive wells is small relative to the total number of wells then this estimate can be expected to be very accurate. As the number of positive wells increases, the accuracy and reliability of the estimate becomes worse. However, most specimen types that would most benefit from rapid detection, such as blood, generally have microorganism counts of less than 10 cfu/ml. After dilution with media less than 10% of the wells would be positive.

Additionally, the presence of more than one type of microorganism in the original sample is a big problem for most systems. This is an important and frequent occurrence in blood culture. Polymicrobial bacteremia has been reported in as many as 18% of septic episodes and has been associated with higher mortality. In the case where the entire sample goes into one bottle, it is very early for rapidly growing organisms, such as *E. coli*, to outgrow any other organisms present. The other organism(s) is (are) either not detected or require an additional 18–24 hours to grow isolated colonies for identification and susceptibility testing.

In the methods of this invention, when small numbers of organisms are present, it is highly likely that each organism goes into a separate well. When several species are present, it can, thus, be expected that each positive well is the result of a single organism and is therefore a pure culture. If one species (such as *E. coli*) dominates the original sample, it would be expected to be the culture in most of positive wells; but would not affect or mask the growth of other species in the remaining positive wells. Thus the detection of multiple microorganisms is greatly simplified.

Further, in cases where the generation time for the microorganism is long, e.g. mycobacteria such as those associated with tuberculosis, the detection time is greatly reduced. This permits quicker diagnoses and permits treatment to begin earlier.

EXAMPLES

The following examples present certain preferred embodiments of this invention, but are not intended to be illustrative of all embodiments.

Example 1

To illustrate the advantage of the method of this invention, a series of calculations were performed to determine the time required to achieve a threshold concentration of $1 \times 10^6$ CFU/ml, for a 8 ml aliquot diluted to 80 ml in culture media, assuming a generation time of 20 or 30 minutes, and a time lag of 30 minutes (1 day in the 12 hour case). The results are presented in Table 1.

TABLE I

| Generation Time | Total CFU In 8 ml Blood (CFU/ml) | Time to Threshold (Min) | | Time Saved |
|---|---|---|---|---|
| | | Con.[a] | Inv.[b] | |
| 20 minutes | 1 (0.125) | 560 | 420 | 140 min |
| | 2 (0.250) | 546 | 420 | 120 min |
| | 8 (1.0) | 500 | 420 | 80 min |
| | 16 (2.0) | 480 | 420 | 60 min |
| | 32 (4.0) | 460 | 420 | 40 min |
| 30 minutes | 1 (0.125) | 825 | 615 | 210 min |
| | 2 (0.250) | 795 | 615 | 180 min |
| | 8 (1.0) | 735 | 615 | 120 min |
| | 16 (2.0) | 705 | 615 | 90 min |
| | 32 (4.0) | 675 | 615 | 60 min |
| | | Days | Days | |
| 12 hours + 1 day lag | 1 (0.125) | 14.25 | 10.75 | 3.5 days |
| | 2 (0.250) | 13.75 | 10.75 | 3 days |
| | 8 (1.0) | 12.75 | 10.75 | 2 days |

TABLE I-continued

| Generation Time | Total CFU In 8 ml Blood (CFU/ml) | Time to Threshold (Min) | | Time Saved |
|---|---|---|---|---|
| | | Con.[a] | Inv.[b] | |
| | 16 (2.0) | 12.25 | 10.75 | 1.5 days |
| | 32 (4.0) | 11.75 | 10.75 | 1 day |

Notes
[a]Conventional system single measurement
[b]Invention using apparatus comprising One hundred twenty (120) 0.666 ml compartments As shown, the system of this invention provides a significant savings in time, especially when the initial concentration of organism is dilute, or when the generation time is long.

Example 2

To evaluate the comparative speed of the method of the instant invention with commercial bacterial detection systems, the system was reproduced by using a microtiter tray. The three systems used are described below.

Fluorescent Microtiter Tray (Invention)

Preparation of Tray

The fluorescent compound tris 4,7-diphenyl-1,10 -phenanthroline ruthenium (II) chloride ($Ru(DPP)_3Cl_2$) was synthesized using the procedure of Watts and Crosby (J. Am. Chem. Soc. 93, 3184 (1971)). A total of 3.6 mg of the compound was dissolved in 2.0 ml dimethyl sulfoxide (D-5879, Sigma Chemical St. Louis Mo.) and the resultant solutions was then added slowly, with stirring, to 1300 ml silicone rubber forming solution (Water Based Emulsion #3-5024, Dow Corning Midland Mich.). A 35 microliter aliquot of the mixture was subsequently dispensed into each well of a 96 well, flat bottom, white microtiter tray (#011-010-7901, Dynatech Chantilly Va.), and the systems was subsequently cured overnight in a low humidity (less than 25% RH), 60° C. incubator. After curing, the trays were washed by either soaking or by filling and emptying each well several times with each of the following reagents; a) absolute ethanol, b) 0.1M phosphate buffer pH 7.2, c) hot distilled water (about 45° C.) and d) ambient temperature distilled water.

Thirty ml of Vacutainer® TSB was inoculated with 5 ml of organism suspension. The broth suspension was then pipetted into a fluorescent tray with a plurality of 250 ul wells. The tray was covered with a lid and placed in a humidified 35° C. incubator. To measure fluorescent levels the tray was placed in a Fluoroskan II fluorometer (480–490 bandpass excitation filter/570 cut-on emission filter). A well was considered positive if it had greater than 50 fluorescent counts above the mean of the 96 wells. From each positive well, 100 ul was removed, diluted, and plated onto TSA plates to verify organism identification. Negative wells were sampled to verify no organisms were present.

Radiometric (14C) BACTEC® 6B Blood Culture Bottle Without Sheep Blood

Using a syringe the bottle containing 14C media, was inoculated with 5 ml of the organism suspension. The bottle was incubated at 37° C. on a shaker and read at intervals using a BACTEC® 460 reader. A bottle was considered positive if it had greater than 0.0075 microcuries of $^{14}CO_2$.

This radiometric level corresponds with a Growth Index Number of 30. BACTEC® bottles were read until the Growth Index Number was above 30 or the change between two consecutive readings was greater than 10. Samples of 100 ul were removed from each bottle and plated to verify organism identification. Control bottles with no organisms were also incubated and sampled.

Radiometric (14C) Bactec® 6B Blood Culture Bottle With Sheep Blood

Using a syringe, 5 ml of defibrinated sheep blood was added to the same BACTEC® bottle as above and mixed. Five ml of the media/blood mixture was then removed and 5 ml of organism suspension was added to the bottle. The bottle was incubated at 37° C. on a shaker and read at intervals using a BACTEC® 460 reader. BACTEC® bottles were read until the Growth Index Number was above 30 or the change between two consecutive readings was greater than 10. Samples were removed from each bottle and plated to verify organism identification. Control bottles with no organism were also incubated and sampled.

Each system was examined using two different organisms, *Escherichia coli* ATCC 25922 and *Pseudomonas maltophila* BBL #7301 (containing 8 ug/ml amikacin). The results are presented in Table II.

TABLE 11

|  | Microtiter Wells | BACTEC® Bottle w/o S.B. | BACTEC® Bottle w/S.B. |
|---|---|---|---|
| *E. COLI* ATCC #25922 | | | |
| # Positive Tests | 11 | 5 | 2 |
| Avg. Detection Time (hrs.) | 8.25 | 12 | 13 |
| Detection Time as Percent of Microtiter Wells | 100% | 145% | 158% |
| *PSEUDOMONAS MALTOPHILA* BBL #7301 with 8 ug/ml Amikacin | | | |
| # Positive Tests | 2 | 4 | 4 |
| Avg. Detection Time (hrs.) | 12 | 41.0 | 40.0 |
| Detection Time as Percent of Microtiter Wells | 100% | 342% | 208% |

E. Coli

Upon subsequent examination, all positive microtiter wells (threshold equals 50 fl. units above the mean) were found to contain pure cultures of *E. coli*. Sampling from various negative wells yielded no organisms. The positive BACTEC® bottles also had pure cultures.

As shown, the time to detection for the microtiter wells is about 45–58% faster than the BACTEC® bottles.

Pseudomonas Maltophila

Upon subsequent examination, all positive microtiter wells (threshold equals 50 fl. units above the mean) were found to contain pure cultures of Pseudomonas. Sampling from various negative wells yielded no organisms. The positive BACTEC® bottle also had pure cultures.

As shown, the Bactec® bottles time to detection was over 200% of the time for the invention.

It is apparent that many modifications and variations of this invention as hereinabove set forth may be made without departing from the spirit and scope hereof. The specific embodiments described are given by way of example only and the invention is limited only by the terms of the appended claims.

What is claimed is:

1. In a method for detecting the presence of a bacteria in a liquid sample which method comprises: incubating said sample under conditions which encourage bacterial growth and monitoring said sample for bacterial growth, the improvement comprising dividing said sample into a plurality of discrete zones prior to said incubation, and separately monitoring each zone for bacterial growth wherein said liquid sample contains a number of colony forming units such that when the sample is divided into said discrete zones, there is less than one colony forming unit per discrete zone.

2. The method of claim 1 wherein the bacterial growth is monitored by colorimetric means.

3. The method of claim 1 wherein the bacterial growth is monitored by fluorometric means.

4. The method of claim 1 wherein the bacterial growth is monitored by nephelometric means.

5. The method of claim 1 wherein the bacterial growth is monitored by infrared means.

6. The method of claim 1 wherein the sample is divided into the plurality of discrete zones separated by physical boundaries.

7. The method of claim 6 wherein the sample is divided into a plurality of discrete zones on a microtiter plate.

8. The method of claim 7 wherein the sample is divided into a plurality of discrete zones by interlocking dividers.

* * * * *